(12) United States Patent
Toth et al.

(10) Patent No.: US 7,068,751 B2
(45) Date of Patent: Jun. 27, 2006

(54) SYSTEM AND METHOD OF DETERMINING A CENTER OF MASS OF AN IMAGING SUBJECT FOR X-RAY FLUX MANAGEMENT CONTROL

(75) Inventors: Thomas L. Toth, Brookfield, WI (US); David M. Hoffman, New Berlin, WI (US)

(73) Assignee: General Electric Company, Milwaukee, WI (US)

(*) Notice: Subject to any disclaimer, the term of this patent is extended or adjusted under 35 U.S.C. 154(b) by 52 days.

(21) Appl. No.: 10/765,583

(22) Filed: Jan. 27, 2004

(65) Prior Publication Data
US 2005/0089138 A1    Apr. 28, 2005

Related U.S. Application Data

(60) Provisional application No. 60/514,711, filed on Oct. 27, 2003.

(51) Int. Cl.
*A61B 6/03* (2006.01)

(52) U.S. Cl. ............................................ 378/20
(58) Field of Classification Search .............. 378/20, 378/205, 8, 95
See application file for complete search history.

(56) References Cited

U.S. PATENT DOCUMENTS

| | | | |
|---|---|---|---|
| 4,181,858 A | 1/1980 | Moore | |
| 4,437,006 A | 3/1984 | Morgan et al. | |
| 4,578,806 A * | 3/1986 | Grass et al. | 378/205 |
| 4,749,863 A | 6/1988 | Casey et al. | |
| 5,165,100 A | 11/1992 | Hsieh et al. | |
| 5,212,437 A * | 5/1993 | Hescht et al. | 378/131 |
| 5,379,333 A | 1/1995 | Toth | |
| 5,386,446 A * | 1/1995 | Fujimoto et al. | 378/20 |
| 5,400,378 A | 3/1995 | Toth | |
| 5,450,462 A | 9/1995 | Toth et al. | |
| 5,457,724 A * | 10/1995 | Toth | 378/205 |
| 5,577,095 A * | 11/1996 | Kobayashi | 378/205 |
| 5,696,807 A | 12/1997 | Hsieh | |
| 5,764,721 A | 6/1998 | Light et al. | |
| 5,822,393 A | 10/1998 | Popescu | |
| 5,867,555 A | 2/1999 | Popescu et al. | |
| 6,067,341 A | 5/2000 | Horiuchi | |

(Continued)

FOREIGN PATENT DOCUMENTS

JP    11-104121    4/1999

(Continued)

OTHER PUBLICATIONS

Rashid-Farrokhi, Liu, & Bernstein, Local Tomography In Fan-Beam Geometry Using Wavelets, 1996.

*Primary Examiner*—Edward J. Glick
*Assistant Examiner*—Chih-Cheng Glen Kao
(74) *Attorney, Agent, or Firm*—Ziolkowski Patent Solutions Group, SC; Michael A. Della Penna; Carl B. Horton

(57) ABSTRACT

A system and method of diagnostic imaging is provided that includes positioning a subject in a scanning bay, comparing a center of mass of the subject to a reference point, and repositioning the subject in the scanning bay to reduce a difference in position between the center of mass of the subject and the reference point. The present invention automatically selects a proper attenuation filter configuration, corrects patient centering, and corrects noise prediction errors, thereby increasing dose efficiency and tube output.

26 Claims, 12 Drawing Sheets

U.S. PATENT DOCUMENTS

| | | |
|---|---|---|
| 6,269,501 B1 | 8/2001 | Li et al. |
| 6,362,479 B1 | 3/2002 | Andreaco et al. |
| 6,459,755 B1 * | 10/2002 | Li ................................. 378/4 |
| 6,501,828 B1 | 12/2002 | Popescu |
| 6,649,914 B1 | 11/2003 | Moorman et al. |
| 6,654,440 B1 | 11/2003 | Hsieh |
| 2002/0094064 A1 * | 7/2002 | Zhou et al. ................. 378/122 |
| 2003/0007603 A1 * | 1/2003 | Lienard et al. ............. 378/207 |
| 2003/0185343 A1 | 10/2003 | Horiuchi |
| 2003/0206614 A1 * | 11/2003 | Kendrick et al. ........... 378/205 |

FOREIGN PATENT DOCUMENTS

| | | |
|---|---|---|
| JP | 2001043993 | 2/2001 |
| WO | WO03/022019 | 3/2003 |

* cited by examiner

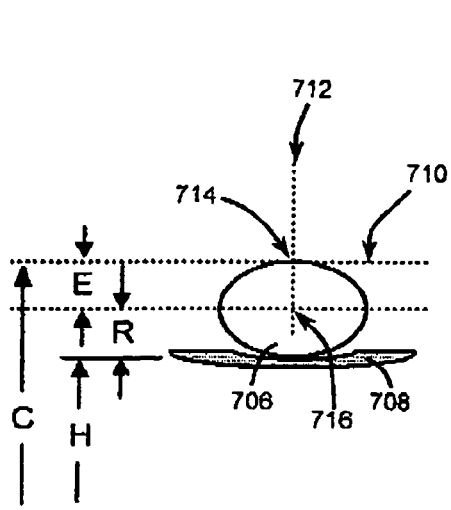
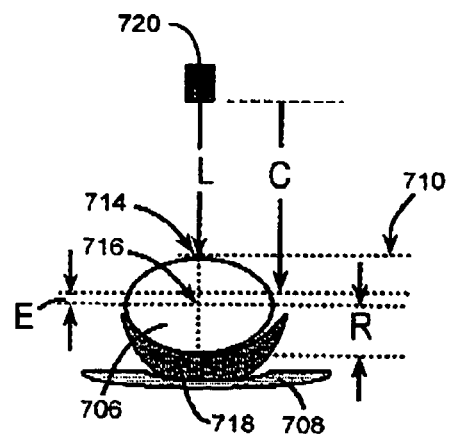
FIG. 18    FIG. 19
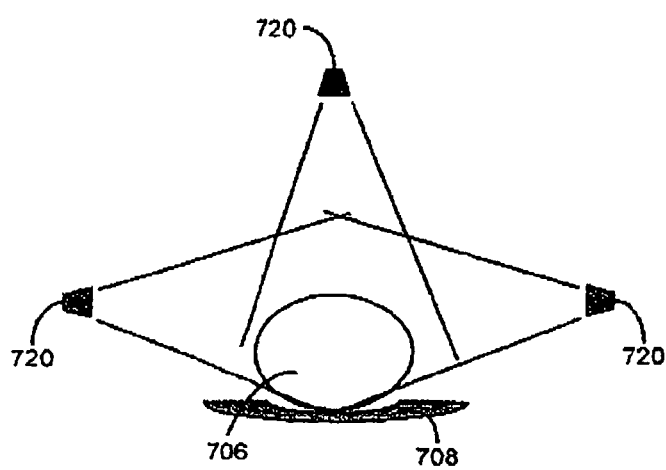
FIG. 20

SYSTEM AND METHOD OF DETERMINING A CENTER OF MASS OF AN IMAGING SUBJECT FOR X-RAY FLUX MANAGEMENT CONTROL

CROSS-REFERENCE TO RELATED APPLICATION

The present invention claims the benefit of U.S. Ser. No. 60/514,711 filed Oct. 27, 2003.

BACKGROUND OF THE INVENTION

The present invention relates generally to diagnostic imaging and, more particularly, to a method and apparatus to optimize dose efficiency by dynamically filtering radiation emitted toward the subject during radiographic imaging in a manner tailored to the position and/or shape of the subject to be imaged.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis and subsequent image reconstruction.

There is an increasing desire to reduce radiation expose to a patient during radiographic data acquisition. It is generally well known that significant radiation or "dose" reduction may be achieved by using an attenuation filter to shape the intensity profile of an x-ray beam. Surface dose reductions may be as much as 50% using an attenuation filter. It is also generally known that radiation exposure for data acquisition from different anatomical regions of a patient may be optimized by using specifically shaped attenuation filters tailored to the anatomical region-of-interest (ROI). For example, scanning of the head or a small region of a patient may be optimized using a filter shape that is significantly different than a filter used during data acquisition from the heart. Therefore, it is desirable to have an imaging system with a large number of attenuation filter shapes available to best fit each patient and/or various anatomical ROIs. However, fashioning an imaging system with a sufficient number of attenuation filters to accommodate the numerous patient sizes and shapes that may be encountered can be impractical given the variances in a possible population. Additionally, manufacturing an imaging system with a multitude of attenuation filters would increase the overall manufacturing cost of the imaging system.

Further, for optimum dose efficiency, i.e. best image quality at the lowest possible dose, the attenuation profile created by the attenuation filter should be particular to the patient. That is, it is desirable and preferred that when selecting a pre-patient or attenuation filter that it be adjusted according to the particulars of the patient, such as the patient's size, shape, and relative position in the bore of the scanner, be taken into account. By taking these and other particulars into consideration, radiation exposure can be optimized for the patient and the scan session.

Known CT scanners use both an attenuation filter and dynamic current modulation to shape the intensity of the x-ray beam incident to the patient. To reduce radiation exposure, the attenuation filer is typically configured to minimize x-ray exposure to edges of the patient where path lengths are shorter and noise in the projection data has a less degrading impact on overall image quality. Accordingly, one such implementation of the attenuation filter is the bowtie filter, which, as a function of form, increases attenuation of x-ray intensity incident upon of the peripheral of the imaging subject. However, improper patient centering and/or bowtie filter selection can significantly degrade image quality and dose efficiency because x-ray attenuation is misapplied to the particulars of the subject. The bowtie filter is aligned with a point of maximum radiation dose or isocenter. The bowtie filter minimizes attenuation of x-ray intensity to isocenter and attenuates radiation significantly with radial distance beyond the center region of the bowtie, because, ideally, the isocenter corresponds to an imaging center of the subject. However, this is not always the case, e.g. when the subject is mis-centered in the scanner.

FIG. 1 illustrates a bowtie filter ideally matched to a patient. Specifically, bowtie filter 10 is aligned within an imaging beam 12 such that an x-ray profile 14 is generated by the incidence of the imaging beam 12 upon the patient 16. However, if the patient 16 is not centered with respect to the bowtie center and the corresponding isocenter, significant image degradation can occur. The degradation is dependent upon a multitude of factors, such as the size of the central region of the bowtie filter, size and shape of the patient, and the amount and direction of patient mis-centering. FIG. 2 illustrates one such example of a bowtie filter opening that is improperly matched to the patient. That is, the bowtie filter 10 is aligned within the imaging beam 12 such that an improper x-ray profile 18 is generated by the incidence of the imaging beam 12 upon the patient 16. Specifically, photon incidence or flux at the edges of the patent may increase image noise to a level that may be prohibitively high for diagnostically valuable images.

Recent improvements in imaging devices include a continuously adjustable bowtie filter having a pair of filtering elements to compensate for factors that may lead to non-ideal imaging. Such a filter is described in U.S. Ser. No. 10/605,789, the disclosure of which is incorporated herein and is assigned to GE Medical Systems Global Technology Co., LLC, which is also the Assignee of this application. Each filter element has a long low attenuating tail section that varies in attenuation power across its length such that as the elements are moved relative to one another, the attenuation of the beam is controlled. Each filter element is dynamically positioned with a dedicated motor assembly. The filter elements may be positioned in the x-ray beam so as to shape the profile of the x-ray beam to match a desired ROI or anatomical point-of-interest.

The filter portions are positionable and adjustable using precision positioners to control the radiation pattern for the patient or the anatomy currently being imaged. However, image degradation may occur if the bowtie opening created is too small for a large patient since useful x-ray needed for imaging is attenuated by the bowtie thereby causing high image noise. As a result, the operator must manually determine the appropriate beam width and position according to size, shape, and positioning of the subject within the scanner bore.

A properly sized bowtie configuration, however, does not ensure acceptable image quality. If the subject is mis-centered, image degradation may still persist. This degradation is typically a result of two factors. First, if subject mis-centering is caused by mis-elevation of the subject with respect to the bowtie filter then the calculation of tube current will result in an underestimate of the subject size. Referring to FIG. 3, a patient 16 is shown mis-centered in an x-ray beam 12. Specifically, the patient 16 is positioned at an improper centering elevation 20 by a centering error 22 below a proper centering elevation or y-position 24. As a result, a portion of the imaging beam 26 is not incident upon the patient 16 and a projection area 28 is understated by an error margin 30 because the patient 16 intercepts fewer rays in the imaging beam 12. As such, when determining tube current with the imaging tube at top-dead-center, as is convention, a lower tube current than actually required for proper imaging will be determined. As a result of the lower tube current, excessive image noise will be present relative to the user's selection. For example, a calculated milliamp (mA) that is 30% lower than actually required for proper imaging occurs for a typical 30 cm×20 cm body mis-centered in elevation by three cm. In such a case, noise introduction is increased by approximately 15% from a properly centered, properly imaged, patient.

Secondly, patient mis-centering with respect to elevation may also position the thickest part of the patient such that x-rays for lateral projections pass through the thickest part of the bowtie which results in over-attenuation of the imaging beam. Referring to FIG. 4, the patient 16 is shown mis-centered within the imaging beam 12 by a centering error 22 below the proper centering elevation 24. As a result, the imaging beam 12 passes through the thickest parts of the bowtie filter 10 and patient 16, as exemplified by projection route 32. Such mis-centering can result in an additional image noise increase by as much as 70%. These errors can cause images of such high noise that the diagnostic value is compromised. Moreover, since traditional CT imaging methods rely on operator input to perfect patient centering, including elevation, elevational patient mis-centering can be common. Furthermore, traditional edge detection methods rely on identifying the center of the patient indirectly by detecting the edges of the patient, which can be particularly susceptible to error.

Additionally, recent advancements in detector technology have increased the desire to control x-ray flux management to within very accurate constraints. For example, photon counting (PC) and energy discriminating (ED) detector CT systems have the potential to greatly increase the medical benefits of CT by differentiating materials such as a contrast agent in the blood and calcifications that may otherwise be indistinguishable in traditional CT systems. Additionally, PC and ED CT systems produce less image noise for the same dose than photon energy integrating detectors and hence can be more dose efficient than conventional CT systems. However, while PC and ED CT systems have the potential to realize numerous advantages over traditional CT detectors, the systems may be impractical for some scan protocols.

Therefore, it would be desirable to design an apparatus and method to automatically control flux by dynamically filtering radiation emitted toward the subject during radiographic imaging in a manner tailored to the position and/or shape of the subject to be imaged so as to optimize radiation exposure during data acquisition. It would be further desirable to have a system that tailors the radiation emitted toward the subject during data acquisition based on a scout scan of the subject. Furthermore, it would be advantageous to have a system and method of controlling x-ray flux management to avoid photon pileup. Additionally, it would be desirable to have a system and method of dynamically adjusting radiation filtering to follow a user defined-region-of-interest. It would also be desirable to have an apparatus to automatically collect patient centering and surface elevation information include a direct method of detecting patient centering. Furthermore, it would be desirable to have a method of accurately determining patient mis-centering within an imaging volume and adjusting the patient position to compensate for the determined mis-centering.

BRIEF DESCRIPTION OF THE INVENTION

The present invention is a directed method and apparatus to optimize radiation exposure that overcomes the aforementioned drawbacks. The present invention includes a method and apparatus to automatically determine a center of mass of an imaging subject. By accurately determining the center of mass of the subject, an x-ray dose received by the subject during imaging may be accurately tailored to the position and/or shape of the subject to be imaged.

In accordance with one aspect of the invention, a method of centering a subject in a medical imaging device is disclosed that includes positioning a subject in a scanning bay, comparing a center of mass of the subject to a reference point, and repositioning the subject in the scanning bay to reduce a difference in position between the center of mass of the subject and the reference point.

In accordance with another aspect of the invention, a computer readable storage medium having stored thereon a computer program representing a set of instructions is disclosed. The instructions, when executed by at least one processor, causes the at least one processor to determine a centroid of a subject, determine a value of mis-centering of the centroid of the subject within a medical imaging device, and adjust a position of the subject within the imaging device to compensate for the value of mis-centering.

In accordance with another aspect of the invention, a method of medical imaging is disclosed that includes positioning a subject in a medical imaging device, determining a value of mis-elevation of the subject, and adjusting an elevation of the subject device to reduce the value of mis-elevation.

In accordance with yet another aspect of the invention, a tomographic system is disclosed that includes a rotatable gantry having a bore centrally disposed therein, a table movable within the bore and configured to position a subject for tomographic data acquisition within the bore, and a high frequency electromagnetic energy projection source positioned within the rotatable gantry and configured to project high frequency electromagnetic energy toward the subject. The tomographic system also includes a detector array disposed within the rotatable gantry and configured to detect high frequency electromagnetic energy projected by the projection source and impinged by the subject and computer. The computer is programmed to determine a centroid of the subject and adjust an elevation of the subject to align the centroid with a reference position.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 18 is an illustration of surface elevation derivation with known patient height data in accordance with the present invention.

FIG. 19 is an illustration of surface elevation derivation with unknown patient height data in accordance with the present invention.

FIG. 20 is a schematic view of a sensor assembly incorporated into an imaging scanner for derivation of patient surface elevation.

DETAILED DESCRIPTION OF THE PREFERRED EMBODIMENT

The present invention is directed to a method and system that automatically determines the patient's size, shape, and centering within an imaging volume and dynamically controls x-ray flux accordingly. Preferably, one or two scout scans together with a plurality of sensors integrally formed with the CT scanner provide patient particulars. The present invention uses the information to provide centering information to the user, allow user input, automatically re-center the patient elevation, correct projection area measurements for dynamic tube current control and select the correct bowtie filter for the optimum dose efficiency.

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to "third generation" CT systems but is equally applicable with a wide variety of CT systems. That is, it is contemplated that the present invention may be utilized with energy integrating, photon counting (PC), and/or photon energy discriminating (ED) CT detector systems.

Specifically, it should be recognized that the present invention provides a technique that controls and effectively limits detector saturation. The technique is adaptable such that it may be tailored to specific the requirements and constraints of a particular detector type and/or detector arrangement. For example, energy integrating detectors, which integrate the amount of x-ray flux recorded during an exposure time, have an inherent flux level tolerance that is relatively high. On the other hand, direct conversion detectors such as photon counting detectors, which actually count each photon as it passes, have a very different, typically lower, flux level tolerance. The present invention provides a dynamically adaptable technique whereby specific flux level tolerances may be observed to avoid detector saturation.

Figure 1:
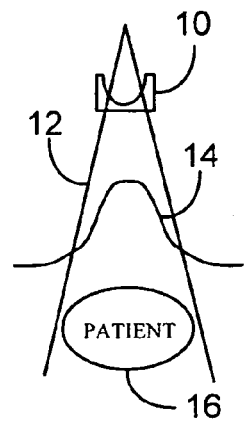
FIG. 1 is a schematic view of a properly aligned attenuation filter assembly and a resulting x-ray profile.
Figure 2:
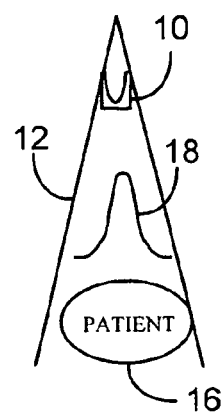
FIG. 2 is a schematic view of an improperly aligned attenuation filter assembly and a resulting x-ray profile.
Figure 3:
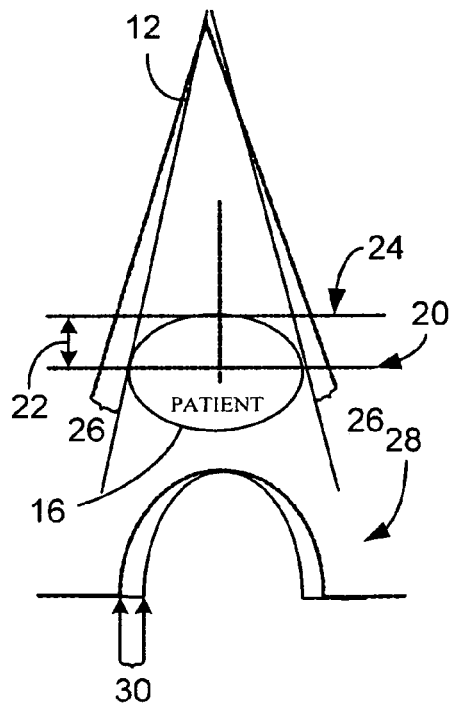
FIG. 3 is a schematic view of an improperly centered patient within an imaging beam and a resulting projection area.
Figure 4:
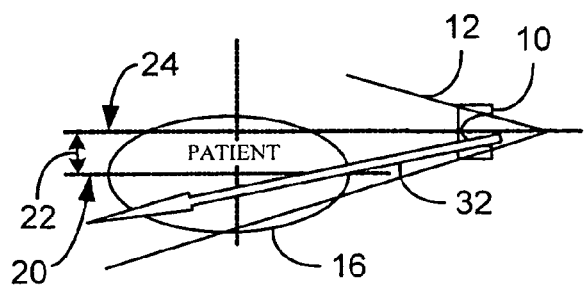
FIG. 4 is a schematic view of an improperly centered patient within an imaging beam.
Figure 5:
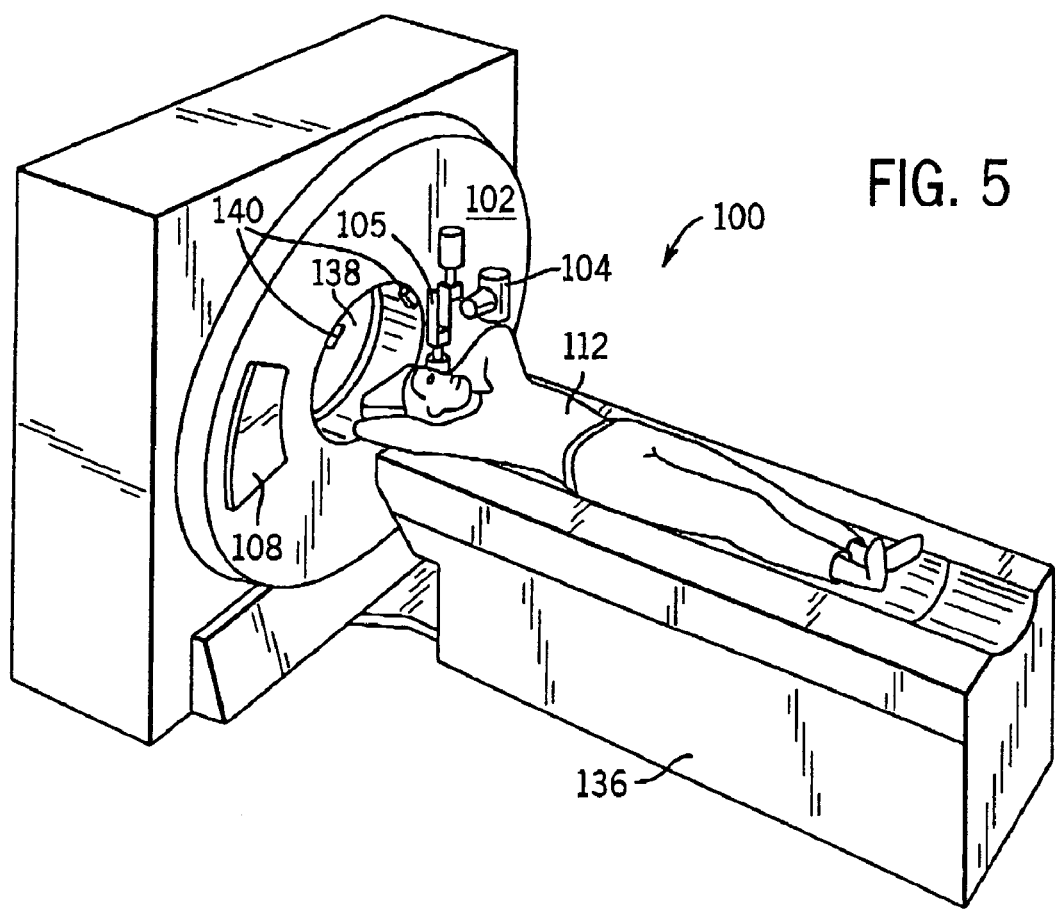
FIG. 5 is a pictorial view of a CT imaging system.
Figure 6:
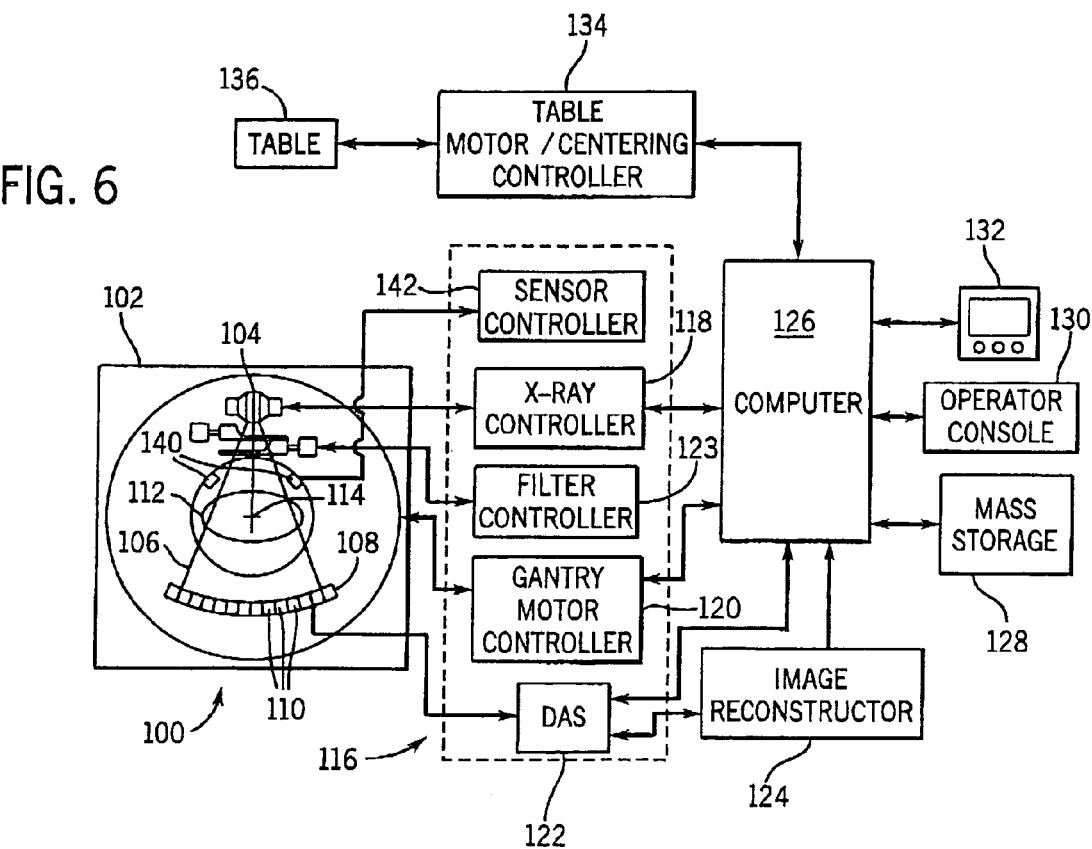
FIG. 6 is a block schematic diagram of the system illustrated in FIG. 5.

Referring to FIGS. 5 and 6, a computed tomography (CT) imaging system 100 is shown as including a gantry 102 representative of a "third generation" CT scanner. Gantry 102 has an x-ray source 104 that projects a beam of x-rays 106 through a filter assembly 105 toward a detector array 108 on the opposite side of the gantry 102. Detector array 108 is formed by a plurality of detectors 110 which together sense the projected x-rays that pass through a medical patient 112. Each detector 110 produces an electrical signal that represents the intensity of an impinging x-ray beam and hence the attenuated beam as it passes through the patient 112. Moreover, the detectors may be photon energy integrating detectors, photon counting, and photon energy discriminating detectors. During a scan to acquire x-ray projection data, gantry 102 and the components mounted thereon rotate about a center of rotation 114.

Rotation of gantry 102 and the operation of x-ray source 104 are governed by a control mechanism 116 of CT system 100. Control mechanism 116 includes an x-ray controller 118 that provides power and timing signals to an x-ray source 104, a gantry motor controller 120 that controls the rotational speed and position of gantry 102, and filter assembly controller 123 that controls filter assembly 105. A data acquisition system (DAS) 122 in control mechanism 116 samples analog data from detectors 110 and converts the data to digital signals for subsequent processing. An image reconstructor 124 receives sampled and digitized x-ray data from DAS 122 and performs high speed reconstruction. The reconstructed image is applied as an input to a computer 126 which stores the image in a mass storage device 128.

Computer 126 also receives commands and scanning parameters from an operator via console 130 that has a user interface device. An associated cathode ray tube display 132 allows the operator to observe the reconstructed image and other data from computer 126. The operator supplied commands and parameters are used by computer 126 to provide control signals and information to DAS 122, x-ray controller 118 and gantry motor controller 120. In addition, computer 126 operates a table motor/table centering controller 134 which controls a motorized table 136 to position patient 112 and gantry 102. Particularly, table motor/table centering controller 134 adjusts table 136 to move portions of patient 112 through and center patient 112 in a gantry opening 138. Sensors 140 are positioned within gantry opening 138 to collect patient position and contour data. Sensors 140 are connected to a sensor controller 142 that controls the operation of sensors 140 and provides the acquired data to computer 126 to be processed.

Figure 7:
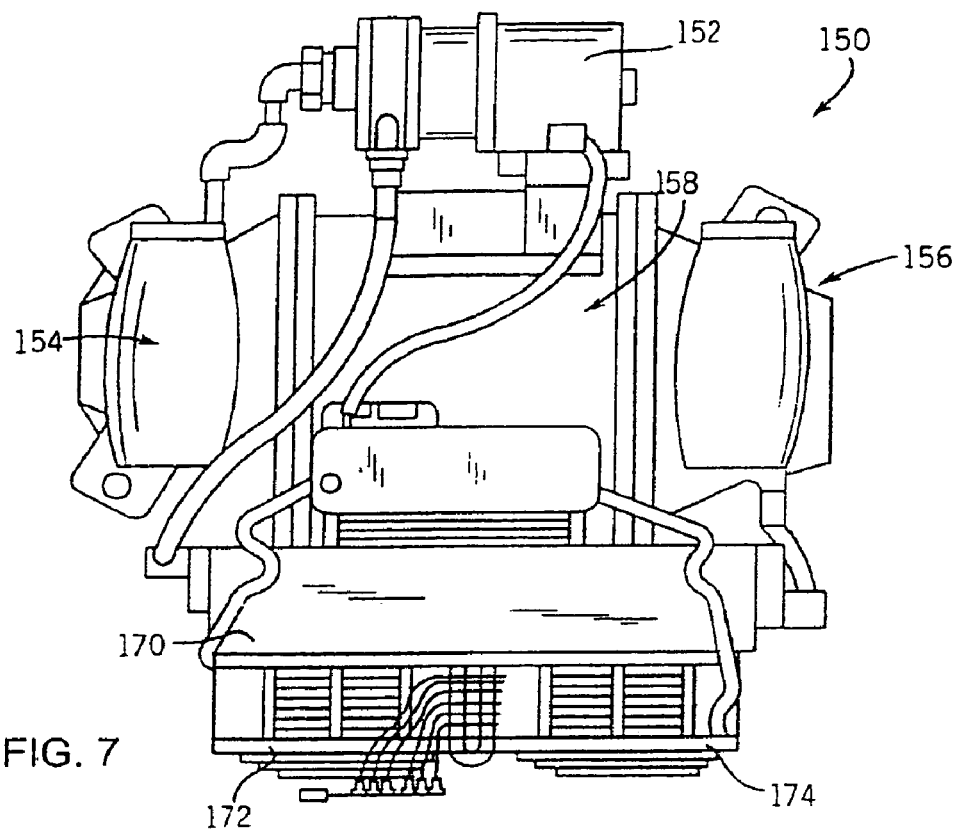
FIG. 7 is a plan view of a representative x-ray system.
Figure 8:
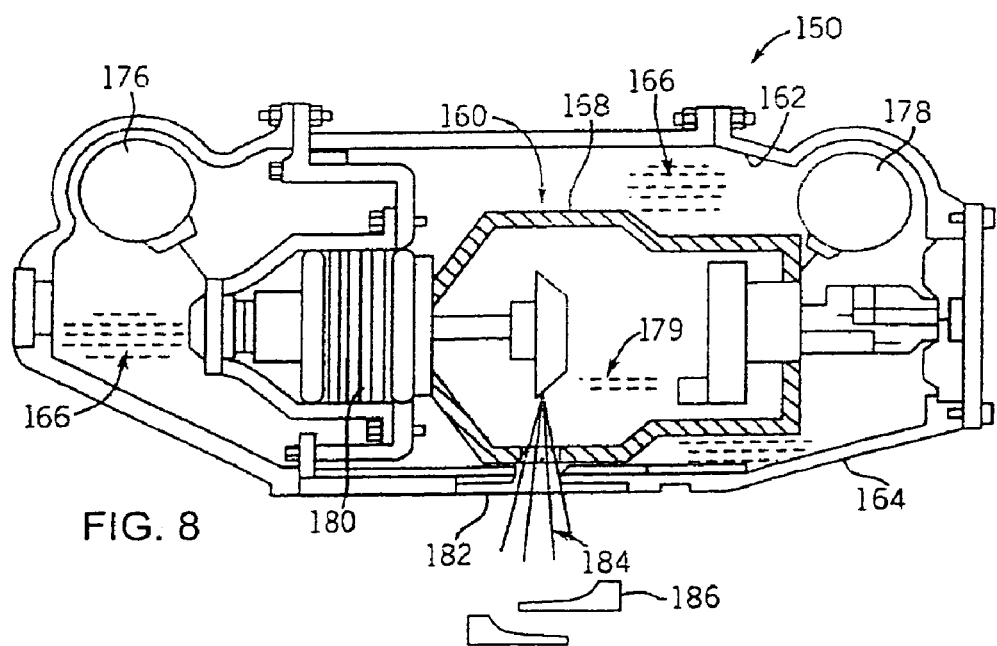
FIG. 8 is a sectional view of a portion of the x-ray system shown in FIG. 5.

As shown in FIGS. 7 and 8, an x-ray system 150 incorporating the present invention is shown. The x-ray system 150 includes an oil pump 152, an anode end 154, and a cathode end 156. A central enclosure 158 is provided and positioned between the anode end 154 and the cathode end 156. Housed within the central enclosure 158 is an x-ray generating device or x-ray tube 160. A fluid chamber 162 is provided and housed within a lead lined casing 164. Fluid chamber 162 is typically filled with coolant 166 that will be used to dissipate heat within the x-ray generating device 160. Coolant 166 is typically a dielectric oil, but other coolants including air may be implemented. Oil pump 152 circulates the coolant through the x-ray system 150 to cool the x-ray generating device 160 and to insulate casing 164 from high electrical charges found within vacuum vessel 168. To cool the coolant to proper temperatures, a radiator 170 is provided and positioned at one side of the central enclosure 158. Additionally, fans 172, 174 may be mounted near the radiator 170 to provide cooling air flow over the radiator 170 as the dielectric oil circulates therethrough. Electrical connections are provided in anode receptacle 176 and cathode receptacle 178 that allow electrons 179 to flow through the x-ray system 150.

Casing 164 is typically formed of an aluminum-based material and lined with lead to prevent stray x-ray emissions. A stator 180 is also provided adjacent to vacuum vessel 168 and within the casing 164. A window 182 is provided that allows for x-ray emissions created within the system 150 to exit the system and be projected toward an object, such as, a medical patient for diagnostic imaging. Typically, window 182 is formed in casing 164. Casing 164 is designed such that most generated x-rays 184 are blocked from emission except through window 182. X-ray system 150 includes an attenuation filter assembly 186 designed to control an attenuation profile of x-rays 184.

As stated, the present invention provides a means to determine patient particulars such as patient size, shape, and centering from one or two scout scans. The information is used to provide centering information to the user, allow user selection of a ROI, automatically center the patient elevation, correct projection area measurements for dynamic tube current control, and select the correct bowtie filter configuration for the optimum dose efficiency. The methods include automatic selection of the proper bowtie filter opening to control the impact of the bowtie filter and patient miscentering on tube current or x-ray flux modulation.

Figure 9:
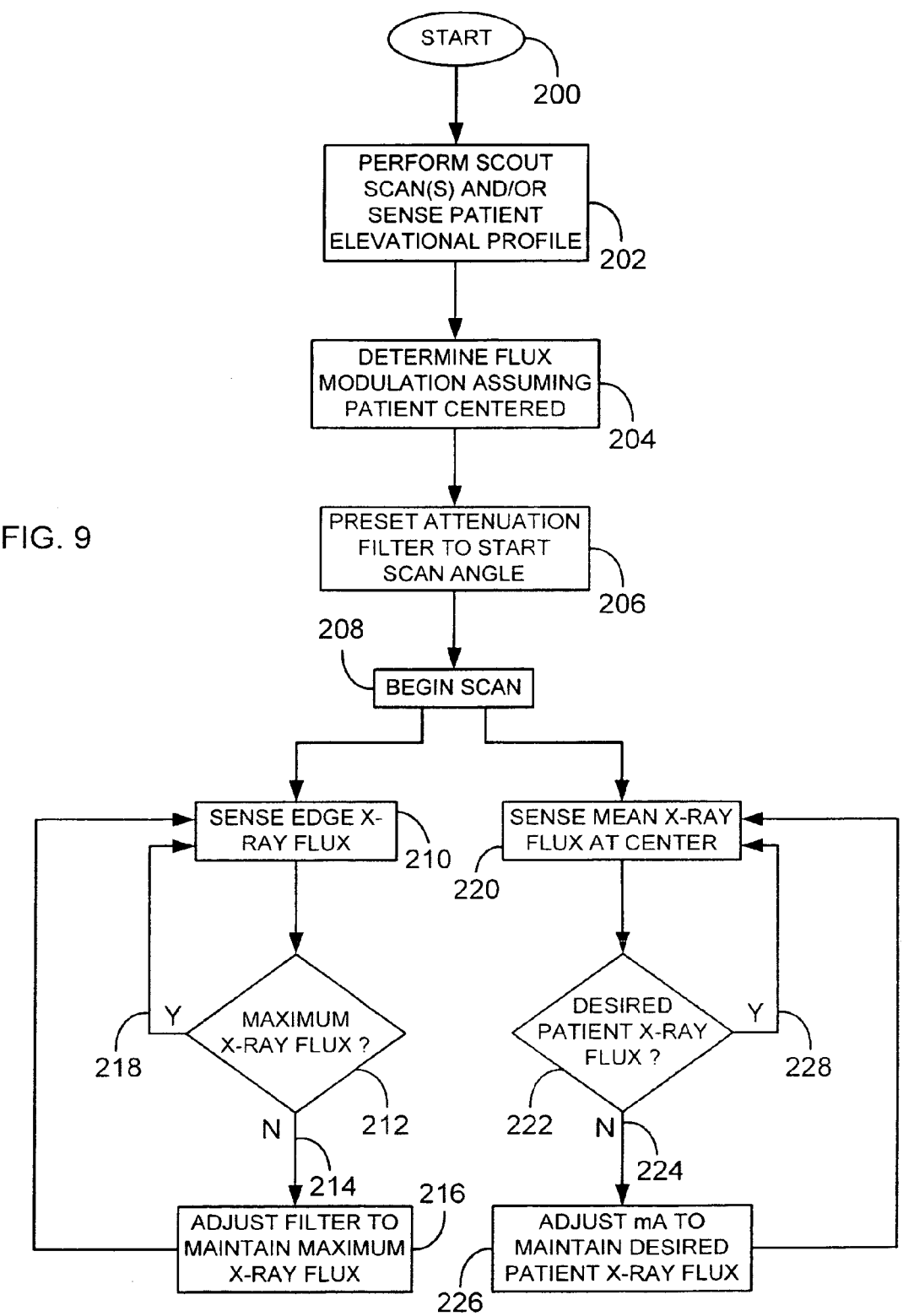
FIG. 9 is a flow chart showing a process in accordance with the present invention that may be implemented with systems of FIGS. 5–8.

Referring now to FIG. 9, a flow chart setting forth the steps of an imaging technique in accordance with the present invention is shown. The technique is particularly tailored for dynamic bowtie and tube current control. The technique begins at 200 with the performance of at least one scout scan and/or sensing a patient elevational profile 202 to determine a required tube current modulation 204 in the x, y and z-directions for a desired image noise assuming a properly centered patient. As will be described in detail, the scout scan(s) may be a lateral scout scan or an anterior-posterior (AP) or posterior-anterior (PA) scout scan. Depending on the orientation of the available scout scan(s), a starting CT scan angle, a location in the z-direction, and positions for the left and right filter segments of the continuously variable bowtie filter, such as that described in commonly assigned patent application U.S. Ser. No. 10/605,789, are selected 206. The starting bowtie (attenuation) filter positions are determined 206 independently for each side, as will be described with respect to FIG. 10.

Once the starting bowtie filter positions have been set 206, scanning begins 208. Bowtie position information is collected and included for each projection during the scan to allow the bowtie attenuation profile to be properly normalized during image reconstruction. Bowtie positioning repeatability is preferably maintained within ten micrometers to allow dynamic calibration and correction of the moving bowtie during patient scanning.

That is, during the scan 208 the information from the scout scan(s) and/or sensed patient elevational profile 202 is/are used to adjust operating parameters. Specifically, a maximum edge x-ray flux is sensed 210 and a closed loop feedback system is utilized to determine whether such is within a select range 212. If it is determined that the maximum edge x-ray flux is outside the selected range 214, the bowtie filter is adjusted to maintain the maximum edge x-ray flux 216. That is, as the maximum flux at the edge of the imaging object increases, an associated filter segment of the bowtie filter is moved toward isocenter. Conversely, if the flux at the edge relative to the center flux is below the selected range, an associated filter segment of the bowtie filter is moved away from isocenter. However, if it is determined that the maximum edge x-ray flux is inside the selected range 218, the bowtie filter is not adjusted and sensing of the maximum edge x-ray flux continues.

At the same time, a mean x-ray flux rate at the central portion of the imaging subject is sensed 220 and a determination of whether the mean x-ray flux rate at the central portion of the imaging subject is outside a selected range is made at 222. If the mean x-ray flux rate at the central portion of the imaging subject is outside the selected range 224, the tube current (mA) is adjusted to maintain the desired mean x-ray flux rate in the central projection region of the imaging subject 226. On the other hand, if the mean flux rate at the central portion of the imaging subject is within the selected range 228, no change to tube current is made and sensing 220 continues.

However, since mA modulation influences the edge flux, it is contemplated that the control of edge flux levels may be done relative to the average central flux level. As such, in accordance with one embodiment of the present invention, the adjustment of bowtie filter toward isocenter 216 and the adjustment of tube current 226 are based on an interdependent consideration of both the sensed maximum flux at the edge of the imaging object 210 and the sensed mean flux rate at the central portion of the imaging object 220.

Furthermore, as will be described, it is contemplated to use a priori positioning for dynamic bowtie positioning with the feedback loop and to use filter positioning moves to prevent photon pileup only when absolute flux limitations are at risk thereby also compensating for the fact that mA modulation influences the edge flux. In this way, the bowtie filter can be positioned for optimum dose efficiency based on imaging subject size, shape, and centering as a first priority whereby positioning for prevention of photon pileup during scanning has precedence. However, it is contemplated that for situations where the central projection region may have the highest x-ray flux, such as for AP projections when scanning legs, for example, adjusting the mA to avoid photon pileup in the center of the projections may be given priority over the tube current modulation objectives.

As will be shown, reliable patient size and centering determinations can be made from projections using two orthogonal scout scans or a single scout scan. However, as will be shown, the present invention includes systems to compensate for the absence of a second scout scan by accurately sensing patient elevational contours. The present invention also includes a method of improved calculations of subject center whereby the centroid (center of mass) is determined from two orthogonal scout projections or estimated from a single scout scan.

The method of FIG. 9 may be utilized to maintain the x-ray flux rates below an absolute maximum limit of a detector. That is, x-ray rates for some detector configurations may be significantly lower than other detectors. Hence, flux rates must be carefully managed to avoid count rate saturation (photon pileup). Since patient attenuation, projection centering error, and desired flux rate levels are known; x-ray flux rates can be controlled by appropriate filter positioning and tube current adjustments using expressions representing the fundamental x-ray physics attenuation and absorption equations.

Figure 10:
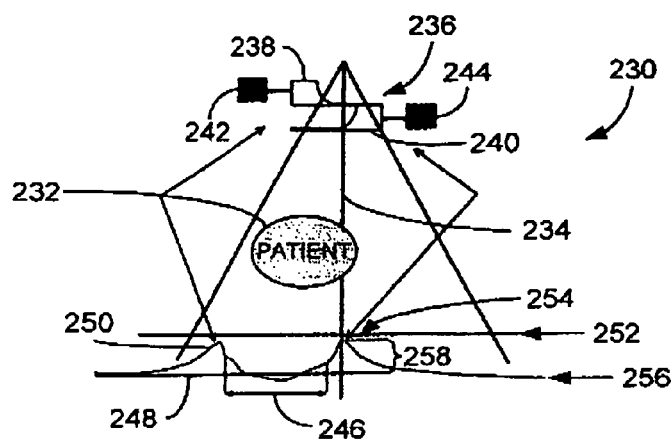
FIG. 10 is a schematic view of an attenuation filter assembly with an improperly centered patient and the resulting flux profile.

Referring now to FIG. 10, an example of a patient mis-centering to the left is illustrated 230. That is, the patient 232 is mis-centered with respect to the isocenter 234 of the x-ray flux passing through a bowtie filter configuration 236. The bowtie filter configuration 236 includes a left bowtie portion 238 and a right bowtie portion 240 that are dynamically adjustable by left control motor 242 and right control motor 244. The bowtie configuration and the tube current are controlled such that a central patient region 246 is within a desired object flux 248 according to a desired image noise. Furthermore, the left bowtie portion 238 is positioned to maintain a left patient edge region flux profile 250 below a max flux limit 252. Similarly, the right bowtie portion 240 is positioned to maintain a right patient edge region flux profile 254 below the max flux limit 252. Accordingly, a filter and patient x-ray flux profile 256 has a relative flux level 258 below the max flux limit 252. As such, flux rates are maintained to remain under the x-ray rates required for specific detector configurations, thereby avoiding photon pileup.

Specifically, the system may be used to overcome limitations, such as photon pileup, which is commonly encountered with the use of photon counting (PC) and photon energy discriminating (ED) CT detectors as opposed to traditional photon energy integrating CT detectors. Photon counting CT systems include detector systems that are capable of distinguishing between photons such that a photon is differentiated from another photon and counted as it is received by the detector. Energy discriminating CT systems are capable of tagging each photon count with its associated energy level. As will be described in detail below, the present invention provides a means to determine an imaging subject's size, shape, and centering and to use this information to provide centering information for automatically re-center patient elevation. Accordingly, as shown in FIG. 10, x-ray flux management may be controlled to maintain a flux profile 250, 254 that is below a max flux limit 252 of a specific detector and its respective flux limits. For example, the flux profile 250, 254 may be specifically controlled to satisfy the requirements of ED or PC CT detectors so as to avoid photon pileup.

Figure 11:
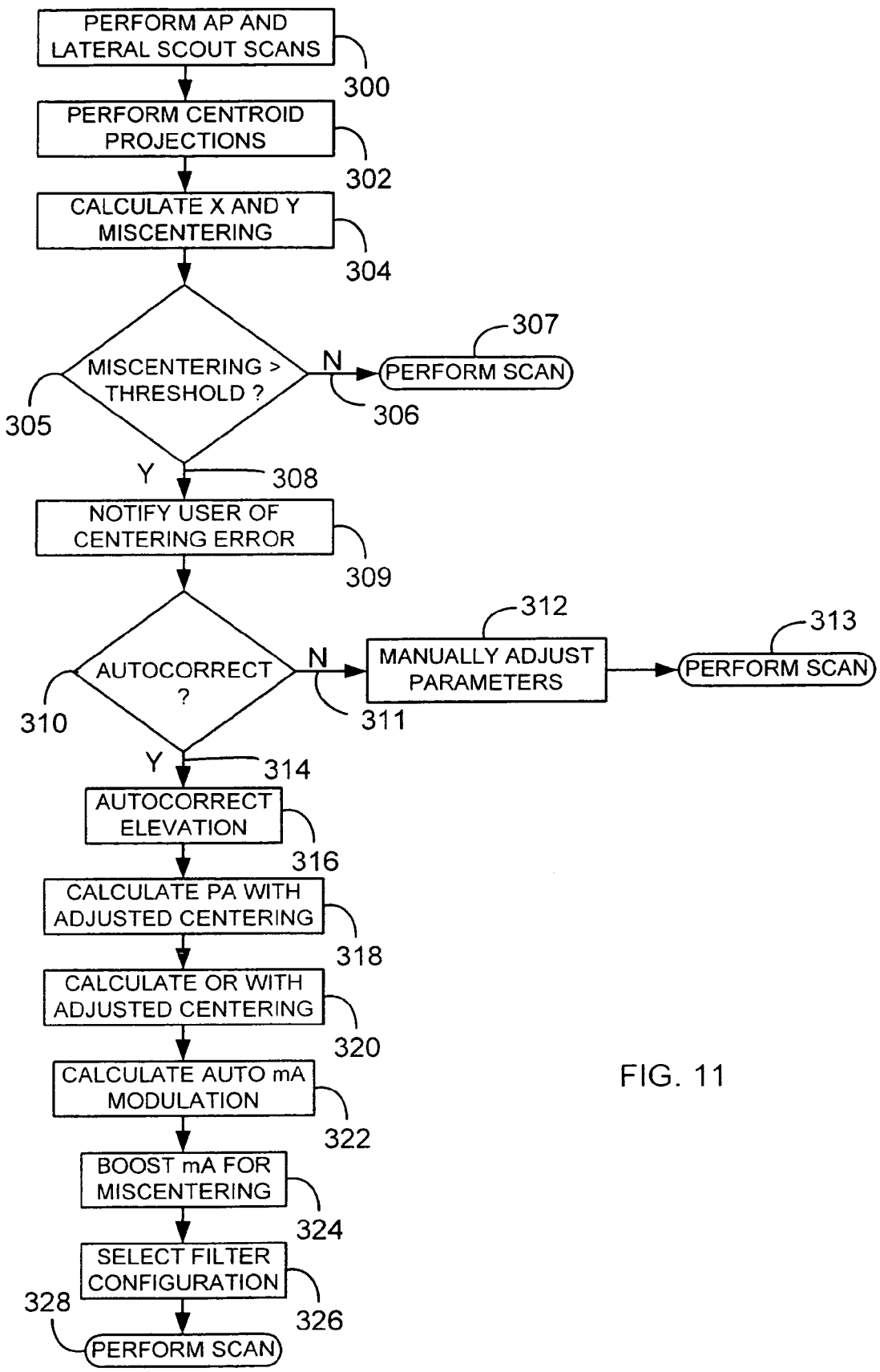
FIG. 11 is a flow chart showing a process for selecting an attenuation filter configuration and tube current modulation scheme utilizing AP and lateral scout scans.

Referring now to FIG. 11, FIG. 11 provides a detailed method for adjusting pre-imaging and imaging parameters. Specifically, two scout scans are performed 300 that include an AP scout scan and a lateral scout scan. From the two scout scans a centroid projection 302 is made. Specifically, the distance of the centroid from a point of reference is made. In a preferred embodiment, the point of reference is isocenter of the x-ray fan beam and the distance of the centroid from isocenter is determined. However, it is also contemplated that the point of reference may be the center of the medical imaging device or the center of the bore of the medical imaging device, or any other stationary point that is readily identifiable. Additionally, it is contemplated that the point of reference may be a map of an ideally positioned imaging subject with similar physical features. In any case, the distance of the centroid from the point of reference is used to geometrically calculate an x and y centering error for the patient relative to a reference position 304. In accordance with a preferred embodiment of the present invention, the reference position is at a center of the scanning bay located in the y-direction. However, it is also contemplated that the reference position may be arbitrarily selected as long as the reference position is fixed with respect to patient position within the CT bore. Having calculated the y-axis patient centering error over the extent of the prescribed CT scan, the system determines the mean center with respect to the reference position, to provide the optimum fixed table height for the duration of the CT scan. The x and y mis-centering is then compared to a threshold 305. Accordingly, a direct determination of the center of the imaging subject is made. That is, by utilizing centroid calculations the center of maximum attenuation that should be positioned in the maximum x-ray field is determined rather than the physical center relative to the edges of the object.

If the mis-centering is less than the threshold 306, indicating that the current position of the patient is within the imaging tolerance of the system, no adjustment is necessary and the system is ready for scanning 307. However, if the mis-centering is greater than the threshold 308, the operator is notified of the centering error 309 and presented with an auto-correction prompt whereby the operator is prompted to accept or reject 310 the table elevation change. However, it is contemplated that operator approval may be bypassed whereby auto-correction is completed without operator approval 310. As such, a fully automated correction system may be implemented. As will be described with respect to FIGS. 11 and 12, should the operator reject the auto-correction 311, the operator may use a graphical indication or other means to enter a user-selected centering correction 312 according to which scanning is performed 313.

Should the operator accept the auto-correction 314, the patient elevation is automatically corrected 316. Additionally, the x and y centering errors are used to correct the projection area (PA) 318. The PA is the sum of the attenuation values of the x-rays that intercept the patient. Therefore, PA is dependent on the distance of the patient from the fan beam x-ray source. By utilizing the accuracy of the centroid calculated x and y centering errors, a corrected PA is directly calculated using geometric equations 318. The PA from both the AP and lateral scouts can be corrected using the centering error determined from the orthogonal scout scan and the average AP scout scan. That is, lateral PA can be used to improve the accuracy of a tube current modulation noise prediction algorithm 322. Additionally, the oval ratio (OR) is directly computed 320 using the projection measure (PM) ratio from the two orthogonal scouts to further improve the accuracy of the tube current modulation noise prediction 322. That is, the tube current is then boosted to compensate for the centroid calculated mis-centering 324.

Once adjustments according to the centroid calculated mis-centering are complete 316–324, the proper bowtie filter configuration is selected 326. Specifically, for a given bowtie filter shape and a given patient size and shape there exists an optimum opening, measured in flat width (FW), that provides the best image quality at the lowest dose. The optimum value is the value of FW that maximizes a quality factor Q as calculated as follows:

$$Q = \frac{KC(a, b, FW)}{N(a, b, FW)\sqrt{D(a, b, FW)}};$$

where:

N is the overall noise in the image or scan data (standard deviation);

D is the dose to the object;

C is the contrast between two materials such as iodine and water (dependent on the spectral characteristics of the system);

K interpolates linearly between $$Q = \frac{1}{\sqrt{N^2 D}} \text{ and } Q = \frac{C}{\sqrt{N^2 D}};$$

a and b are the axes parameters for an ellipse; and

FW is one half of the flat width (i.e. ½ the length of the uniform low attenuation region of the bowtie filter in mm).

In accordance with an alternative embodiment, quality factor may be determined using a single diameter parameter d, where d is the average of a and b. In either case, once the proper bowtie filter configuration is selected 236, the system is ready for scanning 328. As such, the patient table is raised or lowered dynamically during the execution of a helical CT scan to accommodate the changing optimum elevations depending on patient anatomy and centering/mis-centering. Elevation data is included in the scan data header to properly position the views during image reconstruction. If a continuous bowtie is present, the bowtie is positioned dynamically to follow the sineogram of the patient. That is, an attenuation pattern may be utilized that maps a dynamic configuration of the attenuation of the bowtie so as to achieve desired attenuation over time, i.e. during data acquisition.

Figure 12:
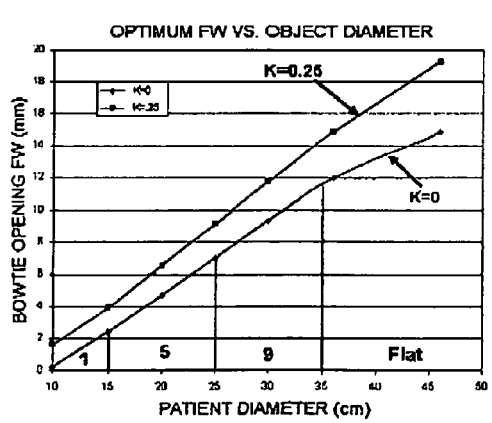
FIG. 12 is a graph of a set of optimum bowtie opening values derived from patient size.
Figure 13:
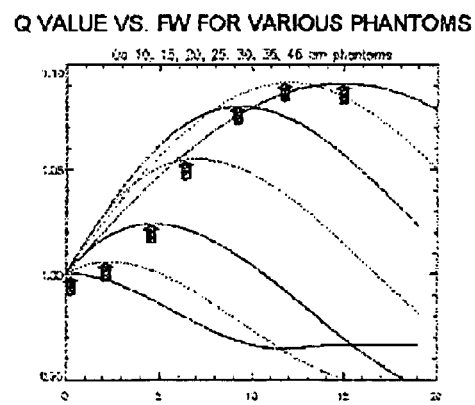
FIG. 13 is a graph of a quality factor versus attenuation filter opening for a plurality of patient sizes.

Referring now to FIG. 12, the optimum bowtie filter opening can be determined experimentally by constructing various phantom sizes and shapes and then scanning the phantoms with various bowtie filters having different FW values, reconstructing images, measuring the noise, dose, and contrast for each case, and fitting a curve to the Q values vs. FW as shown in FIG. 13. The optimum FW value for a given patient size can then be determined by reviewing FW value against the Q value. Specifically, the FW value where Q is at a maximum is the optimum FW value, as illustrated in FIG. 13. The Q values can also be determined by computer modeling using fundamental x-ray physics attenuation and absorption equations to estimate the noise, contrast, and dose in the image for each case. The contrast weighting value K can be chosen between 0 and 1. In the given example, the value of K is zero in order to exclude any benefits of improved object contrast.

From experimental data or simulations the set of optimum bowtie opening values can be determined versus patient or object size as shown in FIG. 12. The relationship is approximately linear and can be represented by the equation FW=0.45 (d−10) for the K=0 assumption where d is the patient diameter in centimeters. Patients with diameters less than 10 cm would use a bowtie opening FW value of zero. As such, optimum bowtie opening FW can be accurately selected given the patient diameter d. The patient diameter can be determined from the PM (amplitude of projection) and a patient density assumption μ. The average PM can be obtained from the orthogonal scout scan pair since d=avg (PM/μ). For the human body, the density assumption μ can be assumed to be 0.2, which is the attenuation coefficient of water, except for the chest and head. For the chest and head, μ can be approximated as 0.14 and 0.24, respectively, due to the density decrease of the lungs and the density increase of the skull.

For CT systems with a continuously variable addressable bowtie, the FW value can be determined directly by the equation, d=avg(PM/μ). On CT systems without an addressable continuous bowtie, the equation can be used to select the nearest optimum bowtie from the selection of available discrete bowtie filters. For example a set of discrete bowtie filters that covers the patient range from infants to large obese adults would typically include bowtie filters with openings having FW values of 1, 5, 9, and a flat filter. From the graph on FIG. 12, the following lookup table can be constructed to automatically select the most optimum discrete bowtie for the patient as follows:

| | DIAMETER: | | | |
|---|---|---|---|---|
| | <15 cm | 15 to 25 cm | >25 to 35 cm | >35 cm |
| BOWTIE FILTER: | FW 1 | FW 5 | FW 9 | Flat |

The optimum filter opening, however, is dependent on how well the patient is centered in addition to the patient's diameter. The effect of patient mis-centering is comparable to a patient radius increase for the projections perpendicular to the mis-centering axis. Hence the proper filter selection is a function of the patient diameter plus the mis-centering and can be determined using the equation, FW=0.45 (d−10+ 2ew), where e is the patient mis-centering error in centimeters and w is a weighting factor or function. The weighting factor is typically 1.0 but could be less than 1.0 to constrain the dose increase that would otherwise result when the bowtie is opened to fully account for the worst case effect of mis-centering. The value of w could also be a function of the object size, shape, and mis-centering to more closely match the behavior of image noise with mis-centering of various size objects.

A discrete bowtie selection can also be obtained by adding the centering error factor (2ew) to the phantom diameter for the lookup table index. For example, from the table, a 24 cm patient with a 3 cm error would be considered a 30 cm diameter and hence, filter FW 9 should be selected instead of FW 5 for the centered case. Furthermore, in the event that tube current modulation is used and the patient is mis-centered in a smaller than optimum bowtie, the mA can be boosted to avoid an unacceptable noise increase in the image.

Figure 14:
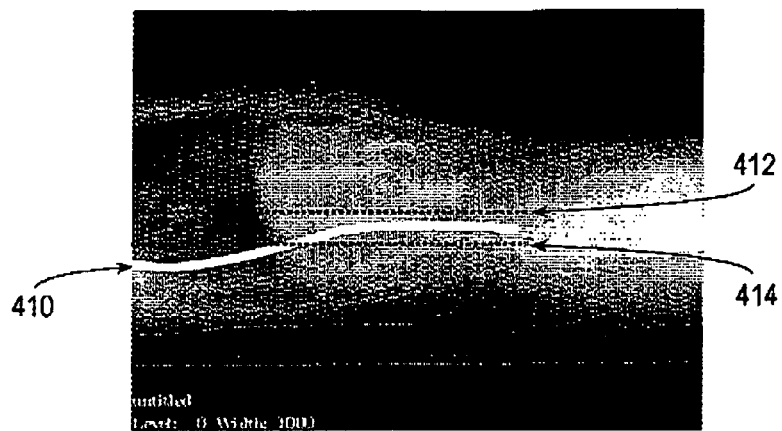
FIG. 14 is an illustration of a lateral scout scan showing an improperly centered patient.

Referring now to FIG. 14, an example of the user interface through which manual entry of a user-selected centering correction 312, FIG. 11, may be entered is shown. In the given example, the user is performing a spine study. In this case, a spine study is optimally centered on the spine 410 instead of the overall attenuation centroid for the patient 412. However, the automatically calculated adjustments will be based upon the mean center of the patient over the scan length and yield the overall attenuation centroid of the patient as the center point 412. Accordingly, the automatically calculated adjustments based on the centroid calculations to compensate for mis-centering are not optimal for the spine study and the operator will choose to manually enter a user-selected centering correction such that recentering is along the mean center of the spine over the scan length 414.

Figure 15:
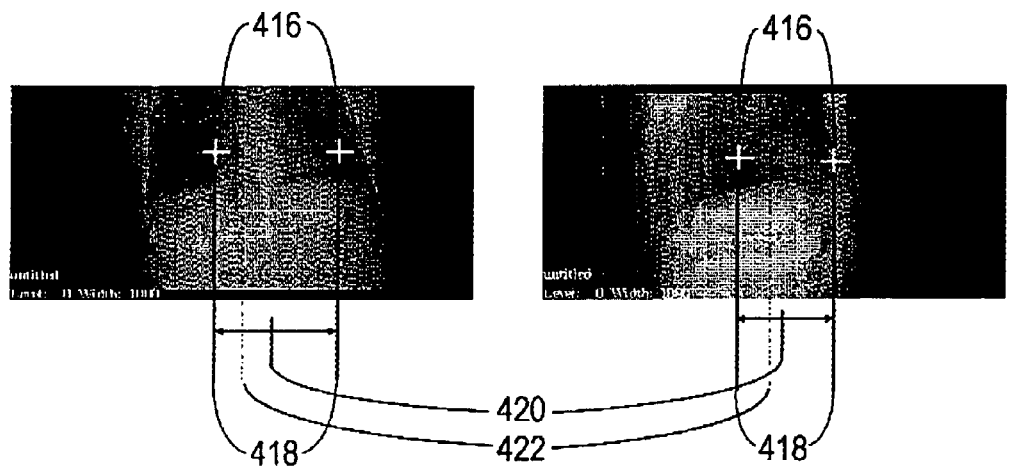
FIG. 15 is an illustration of a user-defined ROI by placement of reference markers on an interface in accordance with one aspect of the present invention.

Referring to FIG. 15, another view of the example of the user interface through which manual entry of a user-selected centering correction may be entered on a pair of scout scans is shown. Through the interface, the user marks the location of the spine or other area of interest on scout scans using cursor markers 416. Via the user-defined cursor markers 416, a diameter of interest 418 is defined that includes a center of interest 420 independent of the centroid calculated isocenter 422.

Accordingly, the patient table may be raised or lowered dynamically during the execution of a CT scan to accommodate the changing optimum elevations depending on patient anatomy to track the user-defined cursor markers. Elevation data is included in the scan data header to properly position the views during image reconstruction. If a continuous bowtie filter is present, the bowtie filter may be controlled dynamically to follow the sineogram of the patient. That is, if the location of a ROI is designated 418 via markers 416, the bowtie filter is dynamically positioned to follow the sineogram of the ROI. This positioning obtains improved image quality for the ROI and reduces dose elsewhere.

Figure 16:
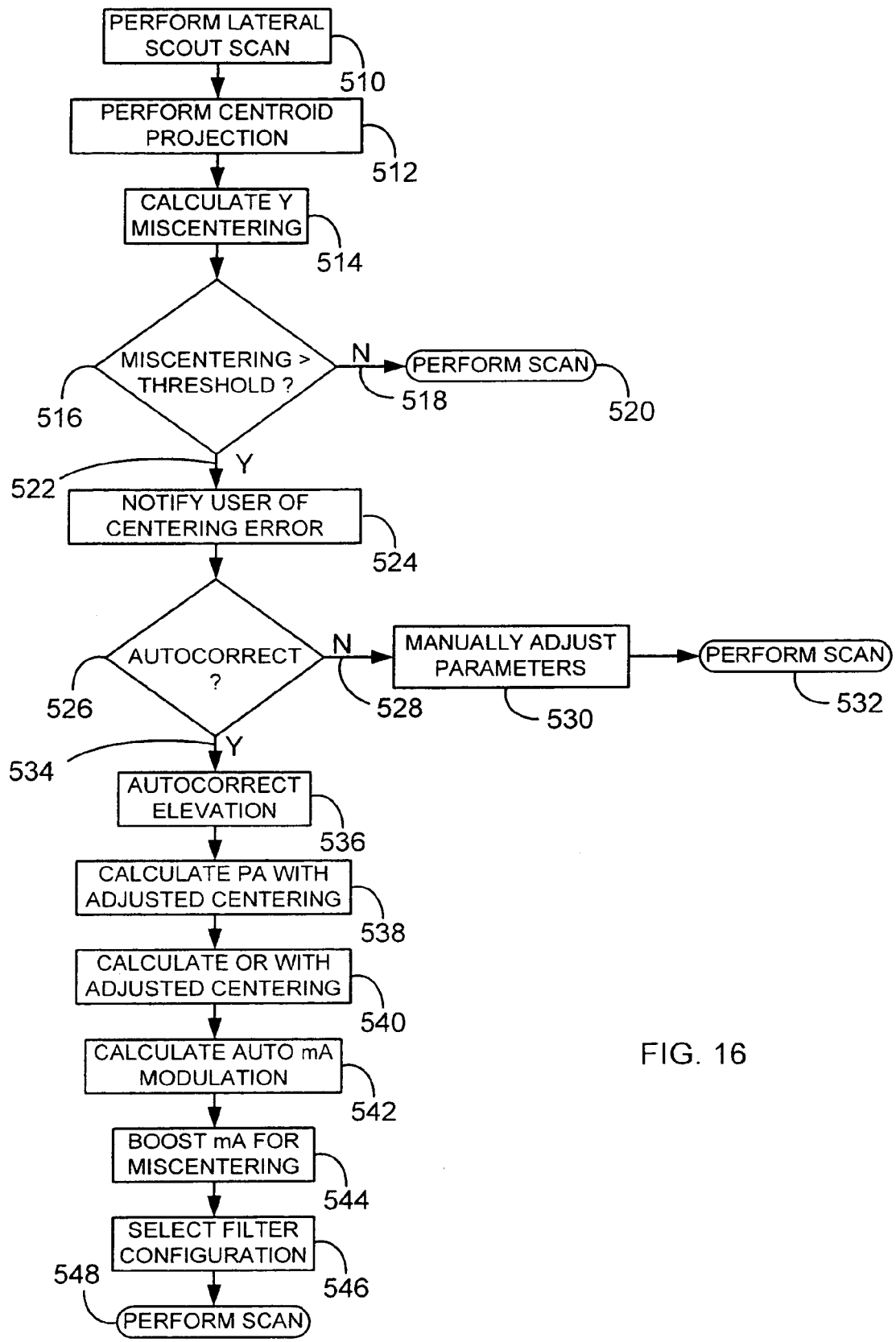
FIG. 16 is a flow chart showing a process for selecting an attenuation filter configuration and tube current modulation scheme utilizing a lateral scout scan.

FIG. 16 illustrates an implementation of the method illustrated in FIG. 11 when only a lateral patient scout scan 510 is available. From the lateral scout scan 510, a centroid projection is made at 512 and y mis-centering is determined relative to a reference position 514 according to the methods previously described. However, since no AP scout scan data is available, x mis-centering is assumed to be zero. The assumption that x mis-centering is 0 provides a reasonable estimation as long as the operator utilizes the edges of the patient table as a guide when positioning the patient in x. Then, having determined the y axis patient centering error over the extent of the prescribed CT scan, the system determines the mean center to provide the optimum fixed table height for the duration of the CT scan. The y mis-centering is then compared to a threshold 516.

If the mis-centering is less than the threshold 518, indicating that the current position of the patient is within the imaging tolerance of the system, no adjustment is necessary and the system is ready for scanning 520. However, if the mis-centering is greater than the threshold 522, the operator is notified of the centering error 524 and presented with an auto-correction prompt whereby the operator is prompted to accept or reject 526 the table elevation change. However, it is contemplated that operator approval may be bypassed whereby auto-correction is completed without operator approval 526. As was described with respect to FIGS. 11 and 12, should the operator reject the auto-correction 528, the operator may use a graphical indication or other means to enter a user-selected centering correction 530 according to which scanning is performed 532.

Should the operator accept the auto-correction 534, the patient elevation is automatically corrected 536. The PA, PM, and OR are calculated 538–540 from the single scout using known methods utilizing y mis-centering calculations. However, since only one PM is available from the single scout scan, the diameter for bowtie selection is determined by the equation, $d=(PM/\mu)(OR+1)/2$ because the OR, by definition, is the ratio of the axis parameters of the elliptical patient model. As such, mA modulation is calculated 542, the mA boost factor is implemented 544, and the appropriate bowtie is selected 546 based on the y-axis centering information using the methods previously described herein. Accordingly, scanning is performed at 548.

Figure 17:
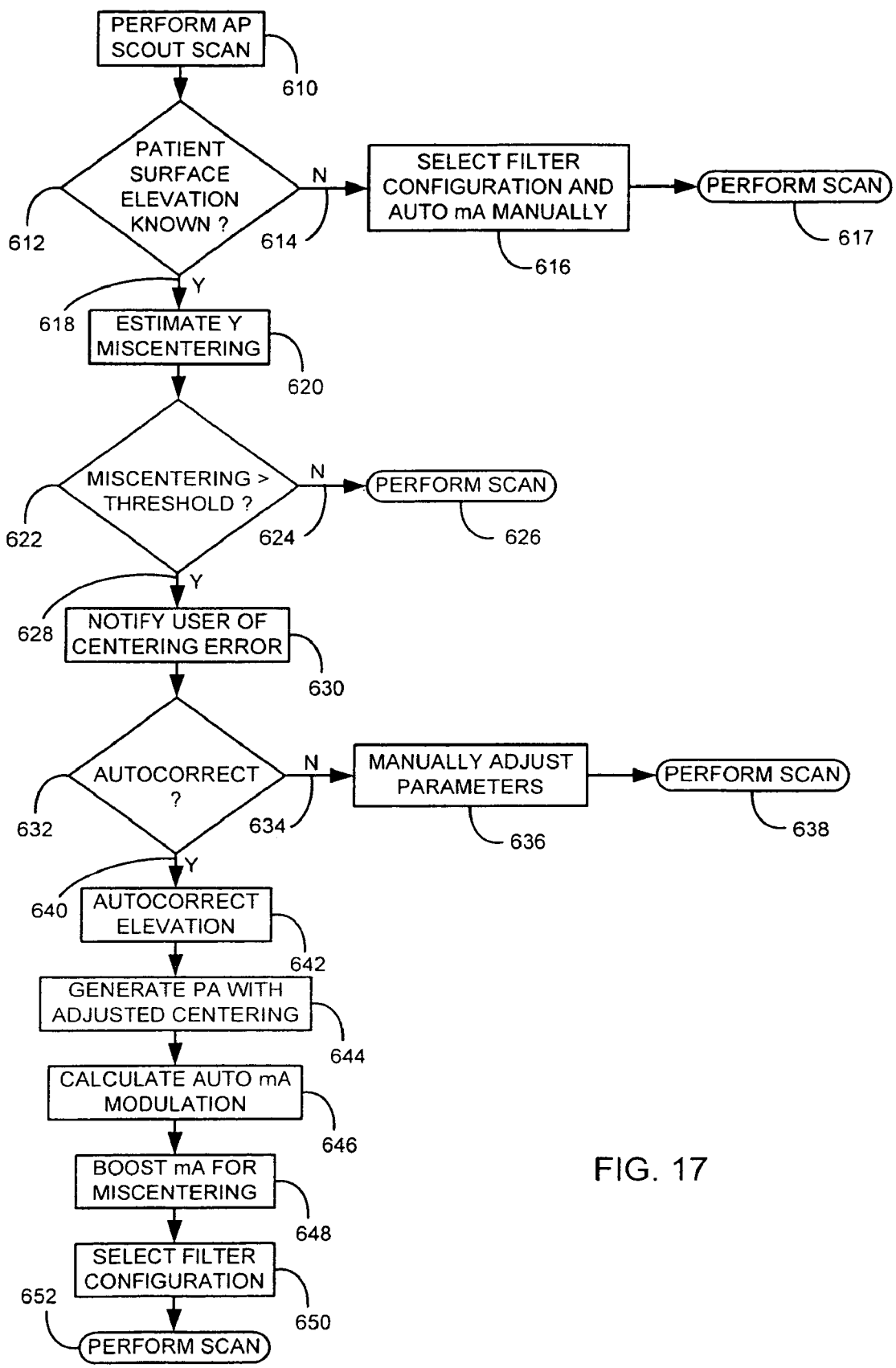
FIG. 17 is a flow chart showing a process for selecting an attenuation filter configuration and tube current modulation scheme utilizing an AP scout scan.

FIG. 17 illustrates an implementation of the method illustrated in FIG. 11 when only an AP patient scout is available. Fundamentally, the method shown in FIG. 17 is substantially similar to that of FIG. 16; however, the y-axis centering error can not be directly determined since it is in the same orientation as the scout projections. Nevertheless, an estimate of the y-axis error relative to a reference position can be made if elevation information relative to the surface of the patient is available.

Once the AP scout scan is complete 610, the system determines whether the surface elevation of the patient is known 612. If the surface elevation of the patient is unknown 614, the operator is prompted to manually select a bowtie filter configuration and calculate tube current per traditional manual methods 616 and a scan is performed 617. However, if the surface elevation of the patient is known or derived 618, as will be described with respect to FIGS. 18–20, an estimation of y mis-centering is performed 620.

The estimation of y mis-centering is then compared to a threshold 622. If the mis-centering is less than the threshold 624, indicating that the current position of the patient is within the imaging tolerance of the system, no adjustment is necessary and the system is ready for scanning 626. However, if the mis-centering is greater than the threshold 628, the operator is notified of the centering error 630 and presented with an auto-correction prompt whereby the operator is prompted to accept or reject 632 the table elevation change. However, it is contemplated that operator approval may be bypassed whereby auto-correction is completed without prior operator approval 632. As was described with respect to FIGS. 11 and 12, should the operator reject the auto-correction 634, the operator uses a graphical indication or other means to enter a user-selected centering correction 636 according to which scanning is performed 638.

Should the operator accept the auto-correction 640, the patient elevation is automatically corrected 642. The PA is then corrected 644 for the estimated y-axis centering error. This is done by direct geometric calculations or as a fitted function of elevation, PA, and OR, as will be described with respect to FIG. 18–20. As such, mA modulation is determined 646, the mA boost factor is implemented 648, and the appropriate bowtie is selected 650 based on the y-axis centering information using the methods previously described herein. Accordingly, the system is ready for scanning 652.

However, it is also contemplated that estimations for PA, PM and mis-centering may be generated from the surface contour of the patient. As such, it is possible to determine mA modulation, boost mA to compensate for patient mis-centering, and select a desired bowtie configuration without the benefit of scout scans. That is, for the selection of the bowtie filter configuration, it is assumed that the patient is centered and the bowtie configuration is selected based on patient size estimated from the PM and density assumption of $\mu$ as previously described herein.

Referring to FIGS. 18, 19, and 20, surface elevation information about the patient can be obtained by various methods. If the patient 706 is resting directly on the patient table 708, as in FIG. 18, the table elevation can be used to determine y-axis centering error. Specifically, with respect to FIG. 18, the table height is known and, as such, the upper horizontal axis 710 of the patient 706 is known or reasonably estimated. Therefore, once the vertical axis 712 is determined, as described above, the upper center 714 of the patient 706 can be determined from the intersection of the upper horizontal axis 710 of the patient 706 and the vertical axis 712. Accordingly, the center 716 of the patient 706 is disposed halfway between the upper center 714 and the table height. Given the determination of these values, table elevation relative to isocenter (E) can be calculated by solving for the equation E=C−R−H, wherein H is the height of the table 708, R is the difference between the center 716 of the patient 706 and the table height, and C is the height of the upper center 714 of the patient 706. Specifically, mis-centering is determined by measuring the offset of the contour projections from isocenter.

However, in cases where the patient 706 is propped up, as in FIG. 19, with pillows or other positioning devices 718, the centering can be determined from a laser or sonic displacement measuring device 720 positioned on the gantry or otherwise disposed on the scanner to locate the top surface of the patient 706. As such, a vector of position information is collected and associated with each scout projection to allow the centering error to be calculated as a function of the z-direction. Specifically, since the center 716 of the patient 706 cannot readily be readily discerned because it is not disposed halfway between the upper center 714 and the table height due to the offset created by the positioning device 718, as shown in FIG. 18, a laser or sonic displacement sensor 720 may be utilized to determine a distance L to the upper horizontal axis 710 of the patient 706. As such, E can be calculated in this case according to: E=R+L−C.

However, referring to FIG. 20, it is also contemplated that a plurality of lasers and/or sonic displacement 720 sensors may be utilized to measure the distance from an array of points to obtain the specific contour of the patient 706. As such, an improved accuracy determination of overall patient contour is achieved.

In any case, the PA can be determined from the external patient contour and the μ for the associated anatomy as described previously herein. The OR is determined directly from the distance measurements or from the PM which can be determined from the μ and patient surface distances. Mis-centering is determined by measuring offset of the contour projections from isocenter.

Once the contour of the patient is known, it is possible to calculate the projection error ratio and fit it to a cubic or other function of elevation, PA, and OR to determine equation coefficients in order to calculate the PA corrected for y-axis centering error according to the following:

$$PA = P/C1 + (C2*E) + (C3*P) + (C4*O) + (C5*E*P) + (C6*E*O) +$$
$$(C7*P*O) + (C8*E^2) + (C9*P^2) + (C10*O^2) +)C11*E*P*O) +$$
$$(C12*E^2*P) + (C13*E^2*O) + (C14*P^2*E) + (C15*P^2*O) +$$
$$(C16*O^2*P) + (C17*O^2*P) + (C18*E^3);$$

wherein:

| Eq coeff | Variable |
| --- | --- |
| C1 | constant |
| C2 | elevation |
| C3 | PA |
| C4 | OVR |
| C5 | elevation * PA |
| C6 | elevation * OVR |
| C7 | PA * OVR |
| C8 | elevation$^2$ |
| C7 | PA$^2$ |
| C10 | OVR$^2$ |
| C11 | elevation * PA * OVR |
| C12 | elevation$^2$ * PA |
| C13 | elevation$^2$ * OVR |
| C14 | PA$^2$ * elevation |
| C15 | PA$^2$ * OVR |
| C16 | OVR$^2$ * elevation |
| C17 | OVR$^2$ * PA |
| C18 | OVR$^3$ | and
E is the table elevation relative to isocenter;
P is the measured projection area;
PA is the projection area corrected for table/patient elevation; and
O is the oval ratio.

It is contemplated that the above-described invention be utilized with "third generation" CT systems as well as a wide variety of other CT-type systems. That is, it is contemplated that the present invention may be utilized with energy integrating, PC, and ED CT detector systems. Furthermore, it is contemplate that the above-described invention may be utilized with non-traditional and non-medical CT applications. For example, it is contemplated that the above-described invention may be utilized with a non-invasive package/baggage inspection system, such as the system shown in FIG. 21.

Figure 21:
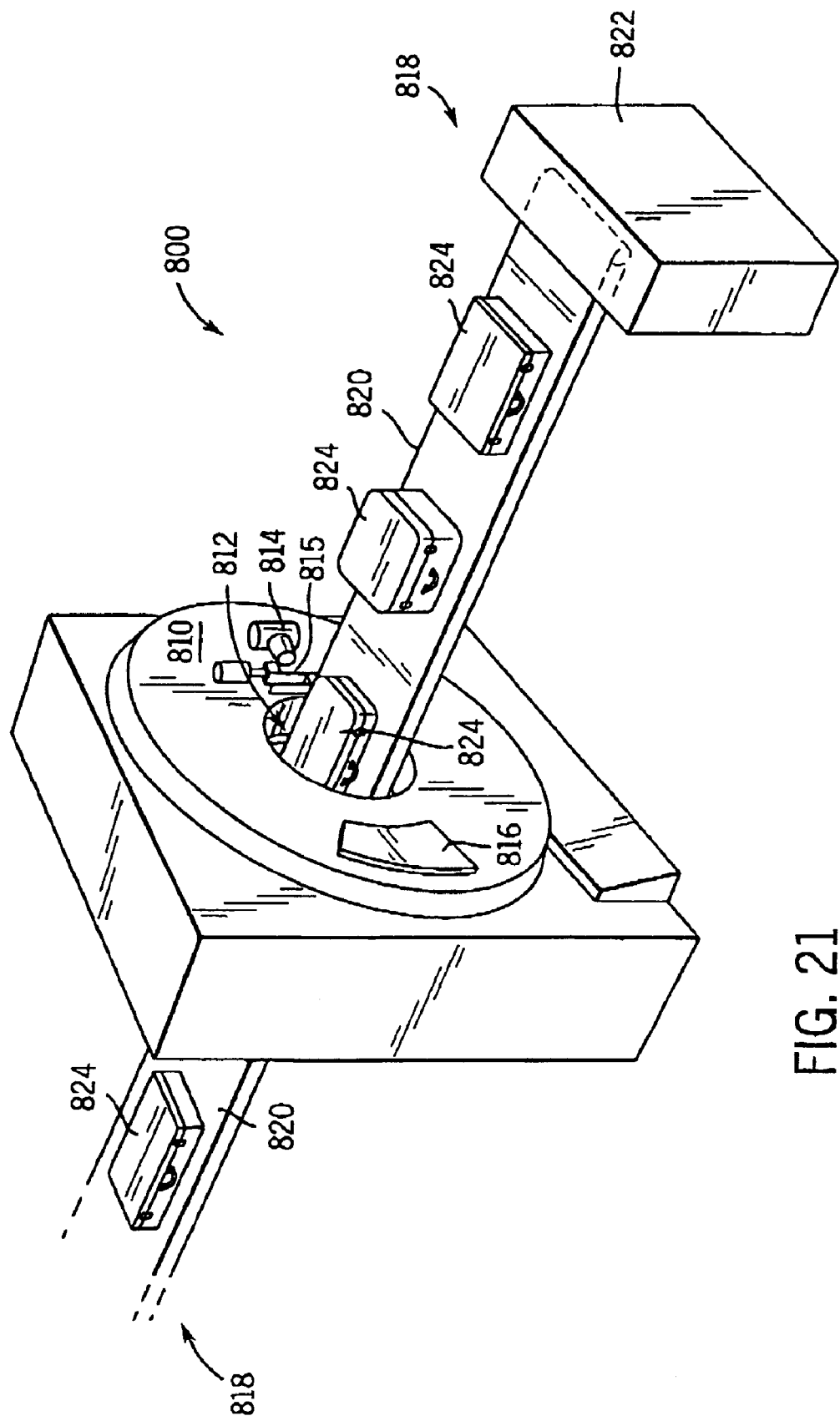
FIG. 21 is a pictorial view of a CT system for use with a non-invasive package inspection system.

Referring now to FIG. 21, package/baggage inspection system 800 includes a rotatable gantry 810 having an opening 812 therein through which packages or pieces of baggage may pass. The rotatable gantry 810 houses a high frequency electromagnetic energy source 814 aligned with an attenuation filter 815 as well as a detector assembly 816. A conveyor system 818 is also provided and includes a conveyor belt 820 supported by structure 822 to automatically and continuously pass packages or baggage pieces 824 through opening 812 to be scanned. Objects 824 are fed through opening 812 by conveyor belt 820, imaging data is then acquired, and the conveyor belt 820 removes the packages 824 from opening 812 in a controlled and continuous manner. As a result, postal inspectors, baggage handlers, and other security personnel may non-invasively inspect the contents of packages 824 for explosives, knives, guns, contraband, and the like.

Therefore, in accordance with one embodiment of the current invention, a method of diagnostic imaging is disclosed that includes determining a position of a subject in a scanning bay relative to a reference position, automatically adjusting an attenuation characteristic of an attenuation filter based on the determined position of the subject and imaging the subject.

In accordance with another embodiment of the invention, a computer readable storage medium is disclosed that has stored thereon a computer program representing a set of instructions. When the instructions are executed by at least one processor, the at least one processor is caused to receive feedback regarding mis-centering of a subject to be scanned, determine a value of mis-centering of the subject to be scanned, and adjust at least one of an attenuation filter configuration and a subject position based on the value of mis-centering. The processor is then caused to acquire radiographic diagnostic data from the subject.

In accordance with still another embodiment of the invention, a tomographic system is disclosed. The tomographic system includes a rotatable gantry having a bore centrally disposed therein, a table movable within the bore and configured to position a subject for tomographic data acquisition within the bore, and a high frequency electromagnetic energy projection source positioned within the rotatable gantry and configured to project high frequency electromagnetic energy toward the subject. A detector array is disposed within the rotatable gantry and configured to detect high frequency electromagnetic energy projected by the projection source and impinged by the subject and an attenuation filter positioned between the high frequency electromagnetic energy projection source and the subject. A computer is programmed to adjust at least one of an attenuation characteristic of the attenuation filter and a table position based on a specific position of the subject in the bore.

In accordance with yet another embodiment of the invention, a method of centering a subject in a medical imaging device is disclosed that includes positioning a subject in a scanning bay, comparing a center of mass of the subject to a reference point, and repositioning the subject in the scanning bay to reduce a difference in position between the center of mass of the subject and the reference point.

In accordance with another embodiment of the invention, a computer readable storage medium having stored thereon a computer program representing a set of instructions is disclosed. The instructions, when executed by at least one processor, causes the at least one processor to determine a centroid of a subject, determine a value of mis-centering of the centroid of the subject within a medical imaging device, and adjust a position of the subject within the imaging device to compensate for the value of mis-centering.

In accordance with yet another embodiment of the invention, a method of medical imaging is disclosed that includes positioning a subject in a medical imaging device, determining a value of mis-elevation of the subject, and adjusting an elevation of the subject device to reduce the value of mis-elevation.

In accordance with still another embodiment of the invention, a tomographic system is disclosed that includes a rotatable gantry having a bore centrally disposed therein, a table movable within the bore and configured to position a subject for tomographic data acquisition within the bore, and a high frequency electromagnetic energy projection source positioned within the rotatable gantry and configured to project high frequency electromagnetic energy toward the subject. The tomographic system also includes a detector array disposed within the rotatable gantry and configured to detect high frequency electromagnetic energy projected by the projection source and impinged by the subject and computer. The computer is programmed to determine a centroid of the subject and adjust an elevation of the subject to align the centroid with a reference position.

In accordance with one embodiment of the invention, a method of imaging is disclosed that includes positioning a subject in an imaging device, performing at least one scout scan, and marking a user-defined region-of-interest (ROI). An attenuation characteristic of an attenuation filter is then automatically adjusted based on the user-defined ROI.

In accordance with another embodiment of the invention, a tomographic system is disclosed that includes a rotatable gantry having a bore centrally disposed therein, a table movable within the bore and configured to position a subject for tomographic data acquisition, and a high frequency electromagnetic energy projection source positioned within the rotatable gantry and configured to project high frequency electromagnetic energy toward the subject. A detector array is disposed within the rotatable gantry and is configured to detect high frequency electromagnetic energy projected by the projection source and impinged by the subject. An attenuation filter is positioned between the high frequency electromagnetic energy projection source and the subject. A computer is included that is programmed to display a user interface including an illustration of a position of the subject and allow selection of a ROI and determine an attenuation profile of the attenuation filter based on the user-selected ROI.

In accordance with another embodiment of the invention, a computer readable storage medium having stored thereon a computer program representing a set of instructions is disclosed. The instructions, when executed by at least one processor, cause the at least one processor to perform at least one scout scan, display an interface including a reconstructed image from the at least one scout scan and receive user-selection identifying a ROI. The instructions then cause the at least one processor to adjust at least one of an attenuation filter configuration and a subject position based on the ROI.

In accordance with yet another embodiment of the invention, a tomographic system is disclosed that includes a rotatable gantry having a bore centrally disposed therein, a table movable within the bore and configured to position a subject for tomographic data acquisition within the bore, and a high frequency electromagnetic energy projection source positioned within the rotatable gantry and configured to project high frequency electromagnetic energy toward the subject. A detector array is disposed within the rotatable gantry and configured to detect high frequency electromagnetic energy projected by the projection source and impinged by the subject and at least one sensor is included to provide subject position feedback.

In accordance with another embodiment of the invention, a computer readable storage medium is disclosed having stored thereon a computer program representing a set of instructions. When the instructions are executed by at least one processor, the at least one processor is caused to receive feedback regarding a subject position from at least one sensor of an imaging device and determine a centering error from the feedback.

In accordance with one more embodiment of the invention, a method of imaging is disclosed that includes positioning a subject in an imaging device, collecting positioning information of the subject from at least one sensor disposed in proximity of the imaging device, and determining a relative position of the subject within the imaging device from at least the position information.

The present invention has been described in terms of the preferred embodiment, and it is recognized that equivalents, alternatives, and modifications, aside from those expressly stated, are possible and within the scope of the appending claims.

What is claimed is:

1. A method of centering a subject in a medical imaging device comprising the steps of:
   positioning a subject in a scanning bay;
   determining a center of mass of the subject from at least one scout scan and an elevational profile of the subject;

comparing a center of mass of the subject to a reference point; and repositioning the subject in the scanning bay to reduce a difference in position between the center of mass of the subject and the reference point.

2. The method of claim 1 further comprising the step of determining a distance of the center of mass of the subject from an isocenter of a radiographic energy fan beam.

3. The method of claim 1 further comprising the step of determining an x-direction and a y-direction centering error of the subject relative to the reference point.

4. The method of claim 1 wherein the reference point includes one of a center of the medical imaging device and a center of a bore of the medical imaging device.

5. The method of claim 1 further comprising the step of automatically performing the steps of positioning, comparing, and repositioning.

6. The method of claim 1 wherein the step of repositioning includes adjusting an elevation of the subject within the scanning bay.

7. The method of claim 1 further comprising the step of performing at least one scout scan of the subject.

8. The method of claim 7 further comprising the step of acquiring an elevational profile of the subject.

9. The method of claim 7 wherein the at least one scout scan includes at least one of a lateral scout scan and an anterior-posterior (AP) scout scan.

10. The method of claim 1 further comprising the step of automatically aligning the center of mass of the subject with an isocenter of a radiographic energy fan beam.

11. The method of claim 1 further comprising the step of determining an adjusted projection area (PA) from a position of the center of mass of the subject after repositioning.

12. The method of claim 1 further comprising the step of adjusting a tube current modulation of the medical imaging device bases on at least the repositioning.

13. The method of claim 1 further comprising the step of determining the elevational profile of the subject from feedback received from a sensor assembly disposed proximate the scanning bay.

14. A computer readable storage medium having stored thereon a computer program representing a set of instructions, which when executed by at least one processor, causes the at least one processor to:
   determine a centroid of a subject;
   determine a value of mis-centering of the centroid of the subject within a medical imaging device; and
   adjust a position of the subject within the imaging device to compensate for the value of mis-centering;
wherein the at least one processor is further caused to determine the centroid of the subject from at least one of:
   at least two scout scans; and
   at least one scout scan and an elevational profile of the subject.

15. The computer readable storage medium of claim 14 wherein the at least one processor is further caused to determine a distance of the centroid from an isocenter.

16. The computer readable storage medium of claim 14 wherein the at least two scout scans includes at least one a lateral scout scan and at least one anterior-posterior (AP) scout scan and the at least one scout scan includes at least one of a lateral scout scan and an AP scout scan.

17. The computer readable storage medium of claim 14 wherein the at least one processor is further caused to determine a distance of the centroid from an isocenter and geometrically determine an x-direction and y-direction centering error of the subject relative to a reference position.

18. The computer readable storage medium of claim 17 wherein the reference position defines a properly centered subject.

19. The computer readable storage medium of claim 14 wherein the at least one processor is further programmed to adjust an elevation of the subject within the imaging device based on the value of mis-centering.

20. A method of medical imaging comprising the steps of:
   positioning a subject in a medical imaging device;
   determining a relative position of a centroid of the subject;
   performing at least one scout scan from which to determine the centroid of the subject;
   determining a value of mis-elevation of the subject from the relative position of the centroid of the subject; and
   automatically adjusting an elevation of the subject to reduce the value of mis-elevation.

21. The method of claim 20 further comprising the step of receiving feedback as to an elevation of the subject from a sensor assembly proximate to the medical imaging device.

22. The method of claim 20 further comprising the step of adjusting the elevation of the subject according to a difference between an actual elevation of the subject and a desired elevation of the subject.

23. The method of claim 20 further comprising the step of adjusting a lateral position of the subject within the medical imaging device.

24. The method of claim 20 further comprising step of adjusting at least one of position of the subject, a projection area (PA), and a tube current modulation of the medical imaging device to compensate for misalignment between the centroid of the subject and an isocenter.

25. A tomographic system comprising:
   a rotatable gantry having a bore centrally disposed therein;
   a table movable within the bore and configured to position a subject for tomographic data acquisition within the bore;
   a high frequency electromagnetic energy projection source positioned within the rotatable gantry and configured to project high frequency electromagnetic energy toward the subject;
   a detector array disposed within the rotatable gantry and configured to detect high frequency electromagnetic energy projected by the projection source and impinged on the subject; and
   a computer programmed to:
      determine a centroid of the subject; and
      adjust an elevation of the subject to align the centroid with a reference position;
      wherein the computer is further programmed to perform at least one scout scan from which to determine the centroid of the subject.

26. The system of claim 25 wherein the computer is further programmed to determine an adjusted projection area (PA) according to the adjusted elevation of the subject.

* * * * *

UNITED STATES PATENT AND TRADEMARK OFFICE
CERTIFICATE OF CORRECTION

PATENT NO. : 7,068,751 B2 Page 1 of 1
APPLICATION NO. : 10/765583
DATED : June 27, 2006
INVENTOR(S) : Toth et al.

It is certified that error appears in the above-identified patent and that said Letters Patent is hereby corrected as shown below:

Col. 19, line 1 (Claim 1), delete "a center" and substitute therefore -- the center --;

Col. 19, line 36 (Claim 12), delete "device bases on at least the repositioning." and substitute therefore -- device based on at least the repositioning of the subject. --;

Col. 19, line 59 (Claim 16), delete "one a" and substitute therefore -- one --; and Col. 20, line 32 (Claim 24), delete "comprising step" and substitute therefore -- comprising the step --.

Signed and Sealed this

Nineteenth Day of September, 2006

JON W. DUDAS
*Director of the United States Patent and Trademark Office*